(12) United States Patent
Lee et al.

(10) Patent No.: US 10,772,595 B2
(45) Date of Patent: Sep. 15, 2020

(54) METHOD AND APPARATUS FOR DISPLAYING MEDICAL IMAGE

(71) Applicant: SAMSUNG ELECTRONICS CO., LTD., Suwon-si (KR)

(72) Inventors: Gi-tae Lee, Hwaseong-si (KR); Dong-jin Yang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 155 days.

(21) Appl. No.: 15/831,628

(22) Filed: Dec. 5, 2017

(65) Prior Publication Data

US 2018/0160996 A1 Jun. 14, 2018

(30) Foreign Application Priority Data

Dec. 14, 2016 (KR) .................. 10-2016-0170406

(51) Int. Cl.
| | |
|---|---|
| *G06K 9/00* | (2006.01) |
| *A61B 6/00* | (2006.01) |
| *G06F 3/0484* | (2013.01) |
| *G06F 3/0488* | (2013.01) |
| *G16H 30/40* | (2018.01) |
| *G16H 30/20* | (2018.01) |
| *A61B 8/00* | (2006.01) |
| *A61B 34/10* | (2016.01) |

(Continued)

(52) U.S. Cl.
CPC ............ *A61B 6/5247* (2013.01); *A61B 6/463* (2013.01); *A61B 8/463* (2013.01); *G06F 3/04845* (2013.01); *G06F 3/04886* (2013.01); *G16H 30/20* (2018.01); *G16H 30/40* (2018.01); *A61B 5/7264* (2013.01); *A61B 34/10* (2016.02); *A61B 2034/107* (2016.02); *G01R 33/546* (2013.01); *G01R 33/5608* (2013.01)

(58) Field of Classification Search
CPC .................................................. G06F 3/04845
See application file for complete search history.

(56) References Cited

U.S. PATENT DOCUMENTS 9,107,569 B2 * 8/2015 Gupta ................ A61B 1/00009
9,204,938 B2 12/2015 Duhamel et al.
(Continued)

FOREIGN PATENT DOCUMENTS

| EP | 2 883 499 A1 | 6/2015 |
| EP | 2 965 693 A1 | 1/2016 |

(Continued)

OTHER PUBLICATIONS

Communication dated Apr. 1, 2019 issued by the Japanese Intellectual Property Office in counterpart Japanese Application No. 2017-239661.
(Continued)

*Primary Examiner* — Oneal R Mistry
(74) *Attorney, Agent, or Firm* — Sughrue Mion, PLLC

(57) ABSTRACT

A method and an apparatus are provided for displaying a medical image. The method includes displaying a first medical image on a screen, based on a first input that zooms in on or zooms out from a first object in the first medical image, determining first geometry information comprising either one or both of position information and size information of the first object, and displaying the first geometry information on a predetermined fixed region of the screen.

19 Claims, 11 Drawing Sheets

(51) Int. Cl.
*A61B 5/00* (2006.01)
*G01R 33/56* (2006.01)
*G01R 33/54* (2006.01)

(56) References Cited

U.S. PATENT DOCUMENTS

| | | |
|---|---|---|
| 9,401,018 B2 | 7/2016 | Lee et al. |
| 2009/0148019 A1* | 6/2009 | Hamada .................... G06T 7/35 |
| | | 382/131 |
| 2013/0039550 A1* | 2/2013 | Blum .................... G06T 7/0014 |
| | | 382/128 |
| 2013/0069946 A1* | 3/2013 | Venon .................... A61B 5/00 |
| | | 345/428 |
| 2014/0184587 A1 | 7/2014 | Park et al. |
| 2015/0019356 A1 | 1/2015 | Bagdonas et al. |
| 2016/0350925 A1 | 12/2016 | Moon et al. |
| 2017/0209125 A1* | 7/2017 | Rai ........................ G01B 11/14 |
| 2019/0365350 A1* | 12/2019 | Chiang ................ A61B 8/4427 |
| 2019/0380782 A1* | 12/2019 | McAfee ................ A61F 2/4455 |

FOREIGN PATENT DOCUMENTS

| | | |
|---|---|---|
| JP | 2005-253636 A | 9/2005 |
| JP | 2009-082365 A | 4/2009 |
| JP | 2010-104710 A | 5/2010 |
| JP | 2011-004923 A | 1/2011 |
| JP | 2012-005636 A | 1/2012 |
| JP | 2014-36735 A | 2/2014 |
| KR | 10-2015-0000780 A | 1/2015 |
| KR | 10-2016-0139298 A | 12/2016 |
| WO | 2004/061544 A2 | 7/2004 |
| WO | 2009-107500 A1 | 9/2009 |

OTHER PUBLICATIONS

Communication dated Mar. 17, 2018, issued by the Korean Intellectual Property Office in counterpart Korean Application No. 10-2016-0170406.
Communication dated Jun. 4, 2018, issued by the European Patent Office in counterpart European Application No. 17204028.9.
Communication dated Oct. 15, 2018 issued by the Japanese Patent Office in Counterpart Japanese Application No. 2017-239661.
Communication dated Sep. 24, 2019 issued by the Japanese Intellectual Property Office in counterpart Japanese Application No. 2017-239661.

* cited by examiner

METHOD AND APPARATUS FOR DISPLAYING MEDICAL IMAGE

CROSS-REFERENCE TO RELATED APPLICATION

This application claims priority from Korean Patent Application No. 10-2016-0170406, filed on Dec. 14, 2016, in the Korean Intellectual Property Office, the disclosure of which is incorporated herein by reference in its entirety.

BACKGROUND

1. Field

Methods and apparatuses consistent with example embodiments relate to methods and apparatuses for displaying medical images to display information about an object in the medical images.

2. Description of the Related Art

Medical imaging systems that provide images of living bodies are used in various fields. Examples of a medical imaging system include a magnetic resonance imaging (MRI) system, a computed tomography (CT) system, a positron emission tomography-CT (PET-CT) system, and an ultrasound system.

To effectively diagnose disease and treat a patient, a medical imaging system is used to accurately and efficiently provide a medical image. Accordingly, there is demand for an apparatus for displaying a medical image that may effectively transmit information about an object in the medical image.

SUMMARY

Example embodiments provide a method and an apparatus for effectively providing information about an object in a medical image to a user by displaying the information about the object on a predetermined fixed region of a screen.

According to an aspect of an example embodiment, there is provided a method of displaying a medical image, the method including displaying a first medical image on a screen, based on a first input that zooms in on or zooms out from a first object in the first medical image, determining first geometry information including either one or both of position information and size information of the first object, and displaying the first geometry information on a predetermined fixed region of the screen.

The predetermined fixed region may not affected by a second input that controls a zoom level with respect to the first object, a third input that controls the first medical image to be moved on the screen, and a fourth input that controls the screen to be changed from the first medical image to a second medical image.

The method may further include determining whether an adjacent region located adjacent to the first object and large enough to display the first geometry information exists in the first medical image, and displaying the first geometry information on the adjacent region instead of the predetermined fixed region, in response to the adjacent region being determined to exist in the first medical image.

The position information of the first object may include any one or any combination of relative position information between a reference position and a first position of the first object in the first medical image, relative position information between the first object and a neighboring object around the first object, and absolute position information of the first object.

The displaying of the first geometry information may include, based on the first medical image being enlarged on the screen and a whole or a part of the first object not being displayed on the screen, continuously displaying the first geometry information on the predetermined fixed region.

The method may further include adjusting an amount of the first geometry information that is displayed, based on a degree to which the first medical image is enlarged on the screen.

The displaying of the first geometry information may include, as the first object is moved in real time, updating the first geometry information, and displaying the first geometry information that is updated, on the predetermined fixed region.

The predetermined fixed region may include any one or any combination of an upper portion, a lower portion, a left portion, and a right portion of the screen, and based on the predetermined fixed region including a plurality of predetermined fixed regions, the displaying of the first geometry information includes displaying the first geometry information respectively on the plurality of predetermined fixed regions, according to a preset standard.

The preset standard may be set so that the position information of the first object is displayed on a first predetermined region among the plurality of predetermined fixed regions, and the size information of the first object is displayed on a second predetermined region among the plurality of predetermined fixed regions.

The method may further include obtaining a second medical image including the first object, determining second geometry information of the first object in the second medical image, obtaining a synthesized medical image by synthesizing the first medical image and the second medical image, based on the first geometry information of the first object in the first medical image and based on the second geometry information of the first object in the second medical image, and displaying the synthesized medical image.

The method may further include receiving a second input that selects a second object in the first medical image, determining second geometry information of the second object, and displaying, along with the first geometry information, the second geometry information of the second object on the predetermined fixed region so that the second geometry information of the second object is distinguished from the first geometry information of the first object.

According to an aspect of an example embodiment, there is provided an apparatus for displaying a medical image, the apparatus including a display configured to display a first medical image on a screen, a user input interface configured to receive a first input that zooms in on or zooms out from a first object in the first medical image that is displayed, and a processor configured to control the display to display the first medical image on the screen, based on the first input, determine first geometry information including either one or both of position information and size information of the first object, and control the display to display the first geometry information on a predetermined fixed region of the screen.

The predetermined fixed region may not affected by a second input that controls a zoom level with respect to the first object, a third input that controls the first medical image to be moved on the screen, and a fourth input that controls the screen to be changed from the first medical image to a second medical image.

The processor may be further configured to determine whether an adjacent region located adjacent to the first object and large enough to display the first geometry information exists in the first medical image, and control the display to display the first geometry information on the adjacent region instead of the predetermined fixed region, in response to the adjacent region being determined to exist in the first medical image.

The position information of the first object may include any one or any combination of relative position information between a reference position and a first position of the first object in the first medical image, relative position information between the first object and a neighboring object around the first object, and absolute position information of the first object.

The processor may be further configured to, based on the first medical image being enlarged on the screen and a whole or a part of the first object not being displayed on the screen, control the display to continuously display the first geometry information on the predetermined fixed region.

The processor may be further configured to adjust an amount of the first geometry information that is displayed, based on a degree to which the first medical image is enlarged on the screen.

The processor may be further configured to, as the first object is moved in real time, update the first geometry information, and control the display to display the first geometry information that is updated, on the predetermined fixed region.

The predetermined fixed region may include any one or any combination of an upper portion, a lower portion, a left portion, or a right portion of the screen, and the processor may be further configured to, based on the predetermined fixed region including a plurality of predetermined fixed regions, control the display to display the first geometry information respectively on the plurality of predetermined fixed regions, according to a preset standard.

The user input interface may be further configured to receive a second input that selects a second object in the first medical image, and the processor may be further configured to determine second geometry information of the second object, and control the display to display, along with the first geometry information, the second geometry information of the second object on the predetermined fixed region so that the second geometry information of the second object is distinguished from the first geometry information of the first object.

According to an aspect of an example embodiment, there is provided a non-transitory computer-readable medium storing instructions executable by a processor of an apparatus for displaying a medical image, to cause the processor to display the medical image on a screen, in response to receiving a first selection of a first object and a second object in the medical image that is displayed, display, along with the medical image, geometry information of the first object and the second object, on a predetermined fixed region of the screen, and in response to receiving an input that zooms in on the first object in the medical image that is displayed along with the geometry information of the first object and the second object, enlarge the medical image that is displayed, display the first object in the medical image that is enlarged, and cease display of the second object in the medical image that is displayed, while the geometry information of the first object and the second object is displayed.

The geometry information may include either one or both of a remaining distance until the second object reaches the first object and a movement path of the second object.

The instructions may be executable by the processor to further cause the processor to, in response to receiving a second selection of a third object in the medical image that is displayed, display, along with the medical image, a first distance between the first object and the second object and a second distance between the second object and the third object, on the predetermined fixed region of the screen.

BRIEF DESCRIPTION OF THE DRAWINGS

The above and/or other aspects will become apparent and more readily appreciated from the following description of example embodiments, taken in conjunction with the accompanying drawings in which reference numerals denote structural elements and.

DETAILED DESCRIPTION

Figure 1:
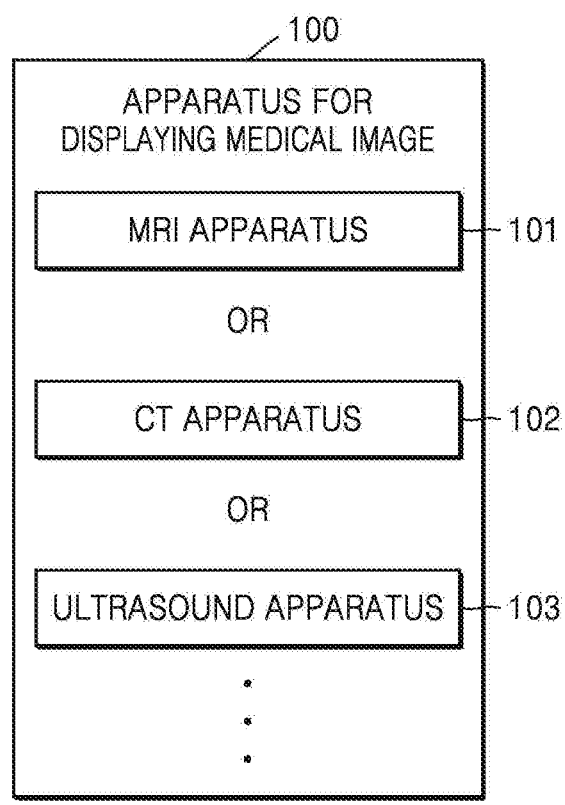
FIG. 1 is a block diagram illustrating an apparatus for displaying a medical image, according to an example embodiment.

The terms used in the present disclosure have been selected from widely used general terms in consideration of the functions in example embodiments. However, these terms may vary according to the intention of any person of ordinary skill in the art, legal precedents, or the advent of new technology. Further, for terms selected by the applicant, the meanings of these selected terms are described in detail in the Detailed Description section. Accordingly, the terms used in the present disclosure are defined based on the descriptions throughout the specification, not by their simple meanings.

When a part may "include" a constituent element, unless specified otherwise, it may not be construed to exclude another constituent element, but instead may be construed to further include other constituent elements. The term "unit" used herein means a software component or a hardware component such as a field-programmable gate array (FPGA) or an application-specific integrated circuit (ASIC), and performs a function. However, the term "unit" is not limited to software or hardware. The "unit" may be formed to be in an addressable storage medium, or may be formed to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units," or may be divided into additional components and "units."

It will be understood that, although the terms first, second, etc. may be used herein to describe various elements, these elements may not be limited by these terms. These terms are only used to distinguish one element from another. For example, a first element could be termed a second element, and, similarly, a second element could be termed a first element, without departing from the scope of the example embodiments. As used herein, the term "and/or" includes any and all combinations of one or more of the associated listed items.

As used herein, the term "image" may refer to multi-dimensional data composed of discrete image elements (e.g., pixels for two-dimensional (2D) images and voxels for three-dimensional (3D) images).

Also, the term "object" used herein may include a human, an animal, or a body part of a human or an animal. For example, the object may include an organ such as the liver, heart, womb, brain, breast, or stomach, or a blood vessel. Also, the "object" may be a phantom. The phantom means a material having a density, an effective atomic number, and a volume that are approximately the same as those of an organism.

Also, the term "user" used herein may refer to, but is not limited to, a medical expert such as a doctor, a nurse, a clinical pathologist, a medical image expert, or a sonographer.

The present disclosure will now be described more fully with reference to the accompanying drawings for one of ordinary skill in the art to be able to perform the present disclosure without any difficulty. The present disclosure may, however, be embodied in many different forms and may not be construed as being limited to the example embodiments set forth herein. Also, parts in the drawings unrelated to the detailed description may be omitted to ensure clarity of the present disclosure. Like reference numerals in the specification denote like elements.

As used herein, the term "and/or" includes any and all combinations of one or more of the associated listed items. Expressions such as "at least one of" when preceding a list of elements, modify the entire list of elements and do not modify the individual elements of the list.

FIG. 1 is a block diagram illustrating an apparatus 100 for displaying a medical image, according to an example embodiment.

According to an example embodiment, the apparatus 100 may be an apparatus for obtaining a medical image and displaying the medical image on a screen. Examples of the apparatus 100 may include, but is not limited to, a magnetic resonance imaging (MRI) apparatus 101, a computed tomography (CT) apparatus 102, an X-ray imaging apparatus, an angiography apparatus, and an ultrasound apparatus 103.

The MRI apparatus 101 is a device for obtaining a cross-sectional image of a portion of an object by expressing an intensity of a magnetic resonance (MR) signal to a radio frequency (RF) signal generated in a magnetic field with an intensity as a contrast.

The CT apparatus 102 may provide a cross-sectional image of an object, and thus has an advantage in that internal structures (e.g., organs such as kidneys and lungs) of the object are not superimposed, unlike a general X-ray imaging apparatus. The CT apparatus 102 may produce a relatively accurate cross-sectional image of the object by obtaining and processing tens of or hundreds of images, each of which has a thickness of, for example, less than 2 mm, per second.

The X-ray imaging apparatus refers to an apparatus for visualizing an internal structure of a human body by allowing X-rays to pass through the human body. The angiography apparatus is an apparatus for visualizing blood vessels (e.g., arteries or veins) of a person to be examined into which a contrast agent is injected through a catheter that is a thin pipe having a thickness of about 2 mm by using X-rays.

The ultrasound apparatus 103 refers to an apparatus for transmitting an ultrasound signal to a predetermined portion in a body from a surface of an object and obtaining an image of the flow of blood or a cross-sectional image of soft tissue by using information about the ultrasound signal reflected from tissue in the body.

According to an example embodiment, the apparatus 100 may be implemented in any of various forms. For example, the apparatus 100 according to the present disclosure may be implemented as a fixed terminal or a mobile terminal. When the apparatus 100 is a mobile terminal, examples of the apparatus 100 may include a smartphone, a laptop computer, a personal digital assistant (PDA), and a tablet PC.

According to an example embodiment, the apparatus 100 may transmit and receive medical image data to and from a hospital server or another medical apparatus in a hospital connected through a picture archiving and communication system (PACS). Also, the apparatus 100 may exchange data with a server according to the digital imaging and communications in medicine (DICOM) standard.

According to an example embodiment, the apparatus 100 may include a touchscreen. The touchscreen may be configured to detect a touch input pressure as well as a touch input position and a touch input area. Also, the touchscreen may be configured to detect a proximity touch as well as a real touch.

The term "real touch" used herein refers to a case in which a touch tool (e.g., a finger or an electronic pen) actually touches the screen, and the term "proximity touch" used herein refers to a case in which a touch tool does not actually touch the screen but approaches a location at a predetermined distance from the screen.

According to an example embodiment, the apparatus 100 may detect a touch gesture of a user on the medical image through the touchscreen. Examples of the touch gesture (e.g., touch input) of the user may include a tap, a touch and hold, a double-tap, a drag, a panning, a flick, a drag and drop, a swipe, and a pinch.

According to an example embodiment, the apparatus 100 may provide, through a graphical user interface (GUI), the whole or a part of an input of the user for selecting an object (e.g., an object of interest, a region of interest, or a point of interest) in the medical image, or an input of the user for controlling the medical image to be displayed.

Figure 2:
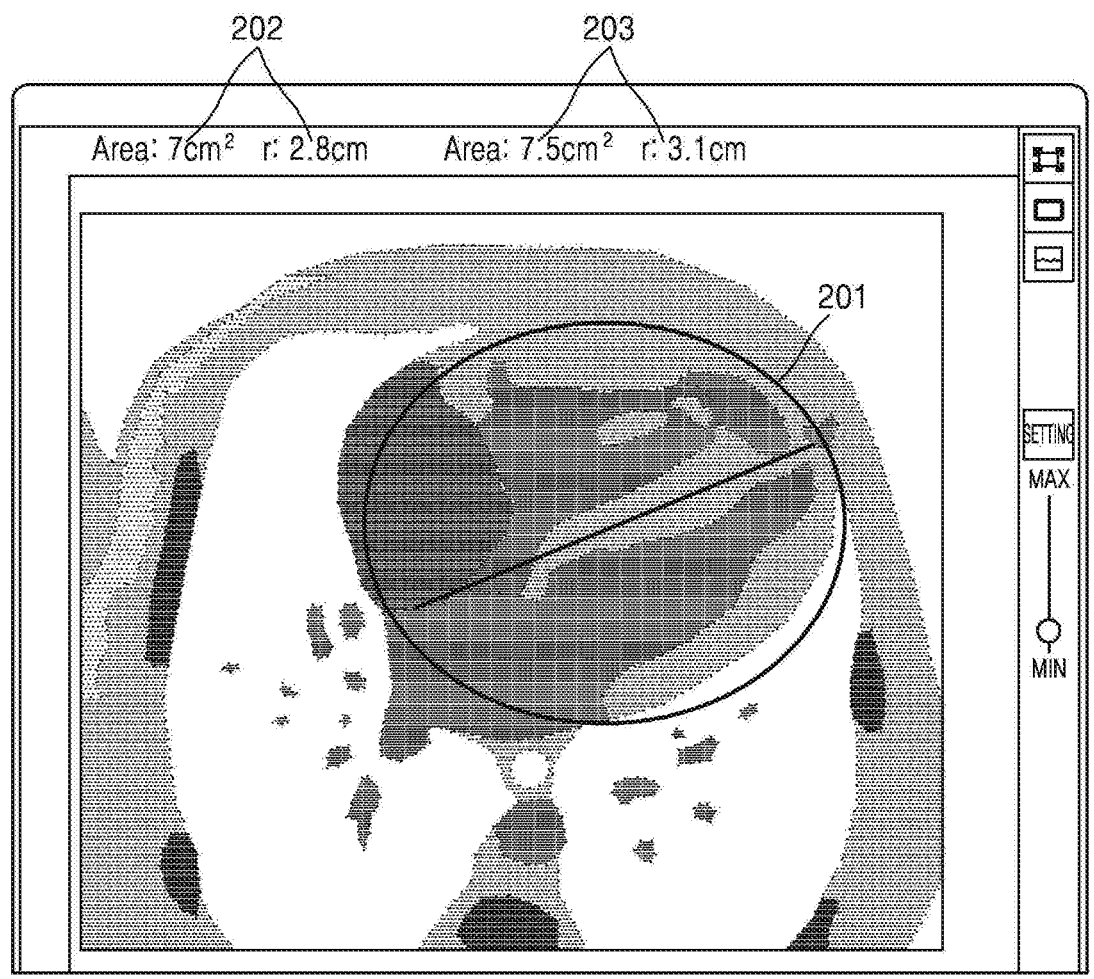
FIG. 2 is a view illustrating a method of displaying a medical image on an apparatus for displaying a medical image, according to an example embodiment.

FIG. 2 is a view illustrating a method of displaying a medical image on an apparatus for displaying a medical image, according to an example embodiment.

The apparatus 100 may display a medical image of an object. Examples of the medical image may include, but are not limited to, an MR image, a CT image, an ultrasound image, and an X-ray image. Also, examples of the medical image may include, but are not limited to, a 2D image, a 3D image, and a four-dimensional (4D) image.

A user may select a first object and a second object as portions of interest in the object. The apparatus 100 may obtain geometry information related to position information or size information of the first object and the second object and may display the geometry information on a screen. The apparatus 100 may display the geometry information of the first object and the second object so that the geometry information of the first object and the second object are superimposed in a first medical image.

Referring to FIG. 2, when a first medical image in which a first object 201 is focused and enlarged is displayed on the screen, a second object and geometry information of the second object may not be displayed on the screen. Accordingly, the apparatus 100 may more efficiently transmit geometry information of an object selected by the user to the user by displaying the geometry information of the object on a predetermined fixed region on the screen, without depending on a medical image displayed on the screen.

As shown in FIG. 2, the apparatus 100 may display the screen on which the first object 201 of the object is focused. In this case, the apparatus 100 may display geometry information 202 and 203 of the first object 201 and the second object, respectively, on a fixed upper portion of the screen that is separately set.

A method by which the apparatus 100 displays the geometry information 202 and 203 about an object in a medical image will now be explained.

Figure 3A:
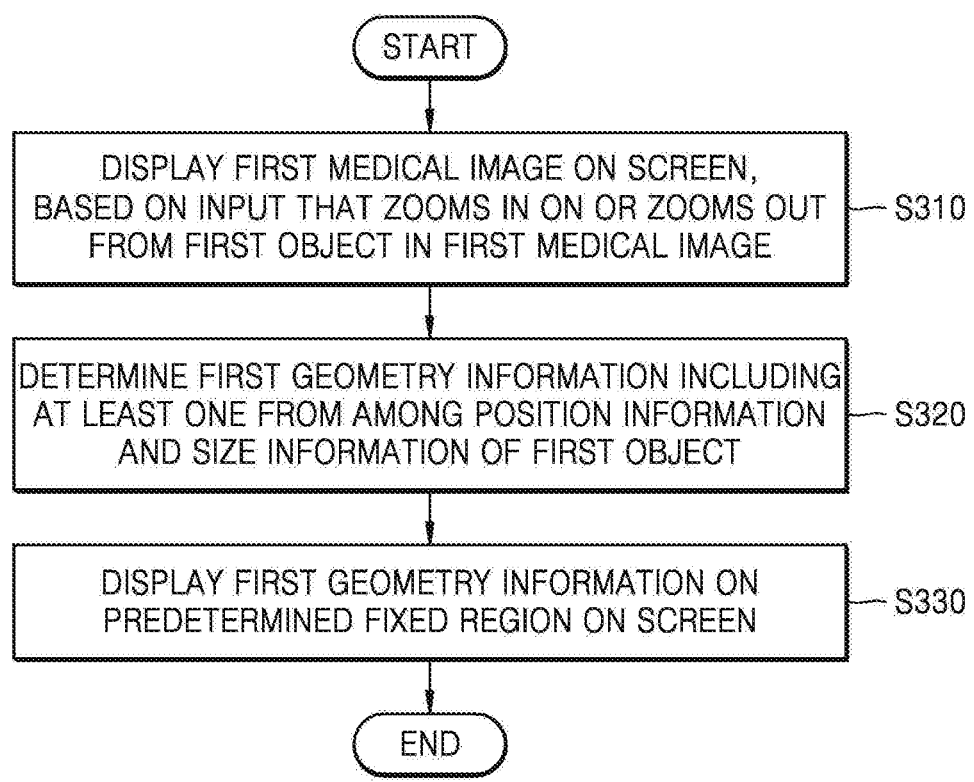
FIGS. 3A and 3B are flowcharts of a method of displaying a medical image, according to example embodiments.

FIG. 3A is a flowchart of a method of displaying a medical image according to an example embodiment.

In operation S310 of FIG. 3A, the apparatus 100 may display a first medical image on a screen, based on an input that zooms in on or zooms out from the first object 201 in the first medical image. The apparatus 100 may obtain a medical image of an object by imaging or scanning the object, or may receive a medical image of the object from an external device.

The external device is a device physically independent from the apparatus 100. Examples of the external device that is a device for obtaining, storing, processing, or using data related to an image of the object may include the apparatus 100, a medical server, a portable terminal, and any computing device for using and processing the medical image. For example, the external device may be a medical diagnostic apparatus included in a medical institution such as a hospital. Also, examples of the external device may include a server for recording and storing medical treatment history of a patient included in the hospital and the apparatus 100 with which a doctor in the hospital reads the medical image.

The apparatus 100 may receive an input that selects the first object 201 in the first medical image. The apparatus 100 may receive a control input that zooms in on or zooms out from the selected first object 201, and may display the first medical image on the screen according to the control input.

According to an example embodiment, the apparatus 100 may receive an input that selects a predetermined region in the first medical image or an input that drags the selected predetermined region. For example, the user may select the first object 201 by clicking and dragging the predetermined region in the first medical image with a mouse. Also, when a display is a touchscreen, the user may select the first object 201 by touching the predetermined region of the first medical image or touching and dragging the predetermined region of the first medical image with a touch tool (e.g., the finger or an electronic pen).

According to an example embodiment, the apparatus 100 may receive a control input that zooms in the first object 201 in the first medical image. In detail, the apparatus 100 may receive an input that selects the first object 201 in the first medical image, and may receive an input that controls the first medical image to be enlarged about the first object 201 and to be displayed on the screen.

According to an example embodiment, the apparatus 100 may receive an input that selects the first object 201 in the first medical image, and may receive an input that controls the first medical image to be reduced about the first object 201 and to be displayed on the screen.

In operation S320, the apparatus 100 may determine first geometry information including at least one from among position information and size information of the first object 201.

The position information of the first object 201 may include any one or any combination of relative position information between a reference position and a position of the first object 201 in the first medical image, relative position information between the first object 201 and a neighboring object of the first object 201, and absolute position information of the first object 201. For example, the relative position information between the reference position and the first object 201 may refer to a distance between the reference position and the position of the first object 201. Also, the relative position information between the first object 201 and the neighboring object around the first object 201 may refer to a distance between the first object 201 and a second object. The second object is a neighboring object around the first object 201. Also, the absolute position information of the first object 201 may refer to position information of a current object in a set coordinate system. Also, the size information of the first object 201 may be information about a length of the first object 201 or a width of the first object 201.

In operation S330, the apparatus 100 may display the first geometry information on a predetermined fixed region on the screen.

The predetermined fixed region may not be affected by an input that controls a zoom level with respect to the first object 201, an input that controls the first medical image to be moved on the screen, and an input that controls the screen to be changed from the first medical image to a second medical image.

The zoom level may be set so that the medical image is enlarged or reduced at a predetermined ratio on the screen. For example, a first zoom level may be set to a level at which the medical image displayed on a current screen is enlarged by 10% and displayed, and a second zoom level may be set to a level at which the medical image displayed on the current screen is enlarged by 20% and displayed. The apparatus 100 may further enlarge and display the medical image displayed on the screen as the zoom level increases. The zoom level may be set by being designated by the user. When the first medical image is enlarged and displayed on the screen according to the control of the zoom level, the whole or a part of the first object 201 may not be displayed on the screen. In this case, the apparatus 100 may display the first geometry information of the first object 201 on the predetermined fixed region on the screen, irrespective of the first medical image displayed on the screen.

Also, the apparatus 100 may receive an input that controls the first medical image to be moved on the screen, and may display the moved first medical image on the screen. In this case, the whole or a part of the first object 201 may not be displayed on the screen. The apparatus 100 may display the first geometry information of the first object 201 on the predetermined fixed region of the screen, irrespective of the first medical image displayed on the screen.

Also, the apparatus 100 may receive an input that controls the screen to be changed from the first medical image to the second medical image, and may display the second medical image on the screen according to the received control input. In this case, the apparatus 100 may display the first geometry information of the first object 201 in the first medical image on the predetermined fixed region of the screen. Also, the apparatus 100 may display second geometry information of the first object 201 in the second medical image along with the first geometry information of the first object 201. Also, the apparatus 100 may display the first geometry information and the second geometry information so that the first geometry information and the second geometry information are distinguished from each other.

That is, the apparatus 100 may display the first geometry information on the predetermined fixed region, without depending on the first medical image displayed on the screen. For example, when the first medical image is enlarged and/or reduced, the predetermined fixed region may maintain its original state without being enlarged and/or reduced along with the first medical image. Also, the predetermined fixed region may be semi-transparently displayed on the screen.

The predetermined fixed region that is a portion of the screen may be designated by the user. Also, the predetermined fixed region may be any one or any combination of an upper portion, a lower portion, a left portion, and a right portion of the screen. Also, the predetermined fixed region may be implemented as a bar on an edge of the screen.

Also, according to whether the first geometry information is displayed, the apparatus may control the bar to be displayed or not to be displayed on the screen.

When a plurality of the predetermined fixed regions exist, the apparatus 100 may distribute the first geometry information and may display the distributed first geometry information on the plurality of regions according to a preset standard. For example, the preset standard may be set, but not limited to, so that the position information of the first object 201 is displayed on a first predetermined region among the plurality of regions, and the size information of the first object 201 is displayed on a second predetermined region among the plurality of regions.

When the first medical image is enlarged on the screen and the whole or a part of the first object 201 is not displayed on the screen, the apparatus 100 may continuously display the first geometry information on the predetermined fixed region.

Also, the apparatus 100 may display the first medical image including the first object 201 on the screen, and then may display the second medical image including the first object 201 on the screen. In this case, the apparatus 100 may display the second geometry information of the first object 201 in the second medical image on the predetermined fixed region. The apparatus 100 may display the first geometry information of the first object 201 in the first medical image and the second geometry information of the first object 201 in the second medical image together.

The apparatus 100 may adjust the amount of display of the first geometry information, based on a degree to which the first medical image is enlarged on the screen. For example, when the first medical image is displayed as an original image on the screen, the apparatus 100 may display the size information of the first object 201 and the position information of the first object 201 on the predetermined fixed region. In contrast, when the first medical image is enlarged and displayed on the screen, the apparatus 100 may display information of neighboring objects around the first object 201 in addition to the size information of the first object 201 and the position information of the first object 201 on the predetermined fixed region. A size of the predetermined fixed region may vary according to the amount of the first geometry information to be displayed.

The apparatus 100 may display the medical image of the object on the screen in real time. The apparatus 100 may track a position of the first object 201 in the first medical image in real time and may display the first geometry information of the first object 201 in real time. That is, as the first object 201 is moved, the apparatus 100 may update the first geometry information of the first object 201 and may display the updated first geometry information on the predetermined fixed region.

Also, the apparatus 100 may obtain a synthesized medical image by synthesizing the first medical image including the first object 201 and the second medical image including the first object 201 and may display the synthesized medical image. The apparatus 100 may synthesize the first medical image and the second medical image, based on the first geometry information of the first object 201 in the first medical image and the second geometry information of the first object 201 in the second medical image.

Also, the apparatus 100 may receive an input that selects the second object in the first medical image, and may determine the second geometry information of the second object. The apparatus 100 may display the second geometry information of the second object on the predetermined fixed region so that the second geometry information of the second object is distinguished from the first geometry information of the first object 201. For example, the apparatus 100 may display the first geometry information of the first object 201 and the second geometry information of the second object in different colors.

According to an example embodiment, an order of operations S310 through S330 may be changed, and some operations may be omitted or added. For example, an operation of displaying the first geometry information so that the first geometry information is superimposed on a region in the medical image, instead of the predetermined fixed region, may be added as described in FIG. 3B below.

Figure 3B:
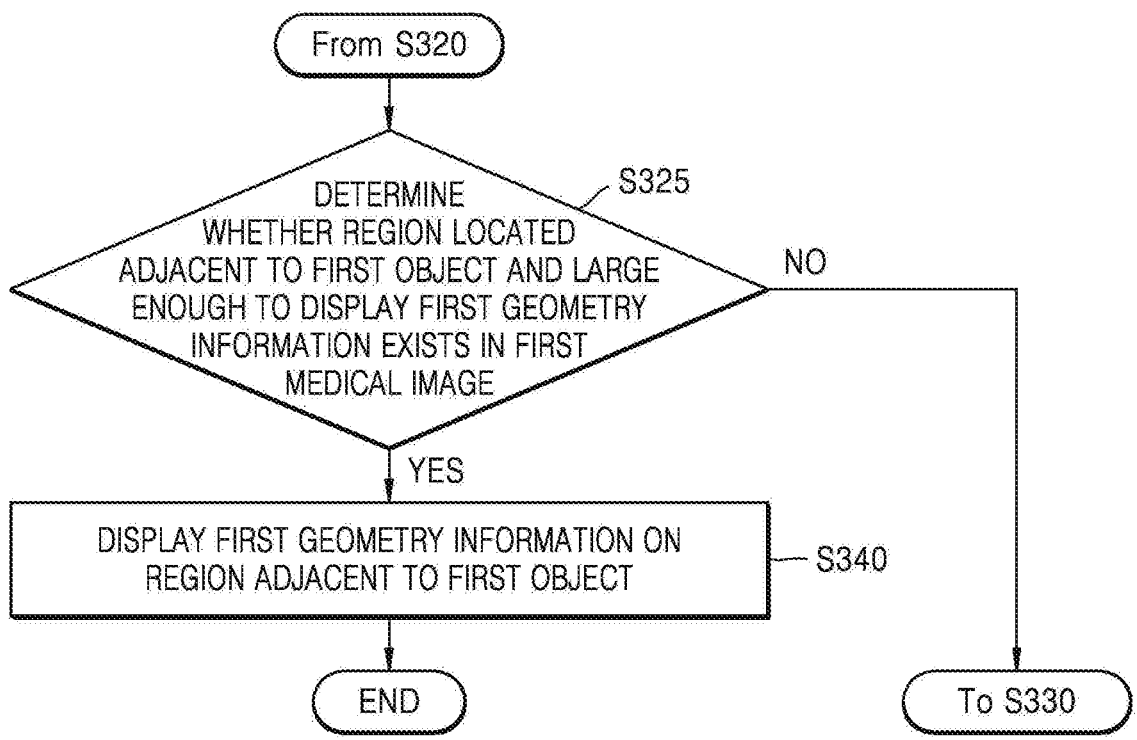

FIG. 3B is a flowchart illustrating a method of displaying a medical image, according to another example embodiment.

In operation S325 of FIG. 3B, the apparatus 100 may determine whether a region located adjacent to the first object 201 and large enough to display the first geometry information exists in the first medical image.

When it is determined in operation S325 that a region located adjacent to the first object 201 and large enough to display the first geometry information exists in the first medical image, the apparatus 100 performs operation S340. In contrast, when it is determined in operation S325 that a region located adjacent to the first object 201 and large enough to display the first geometry information does not exist in the first medical image, the apparatus 100 performs operation S330.

In operation S340, the apparatus 100 may display the first geometry information on the region adjacent to the first object 201. That is, the apparatus 100 may control the first geometry information not to be displayed on the predetermined fixed region of the screen, but to be displayed on the region adjacent to the first object 201.

The method of FIGS. 3A and 3B by which the apparatus 100 displays a medical image may be implemented as a program command executable by various computer elements and may be recorded on a computer-readable recording medium. The computer-readable recording medium may include program commands, data files, or data structures, or combinations thereof. The program commands recorded on the computer-readable recording medium may be designed and configured for example embodiments, or may be well known to and be usable to one of ordinary skill in the art of computer software.

Examples of the computer-readable recording medium may include a magnetic medium such as a hard disk, a floppy disk, or a magnetic tape, an optical medium such as a compact disk-read-only memory (CD-ROM) or a digital versatile disk (DVD), a magneto-optical medium such as a floptical disk, and a hardware device configured to store and execute program commands such as a ROM, a random-access memory (RAM), or a flash memory. Examples of the program commands may include machine language codes made by a compiler and advanced language codes that may be executed by a computer by using an interpreter or the like.

Figure 4A:
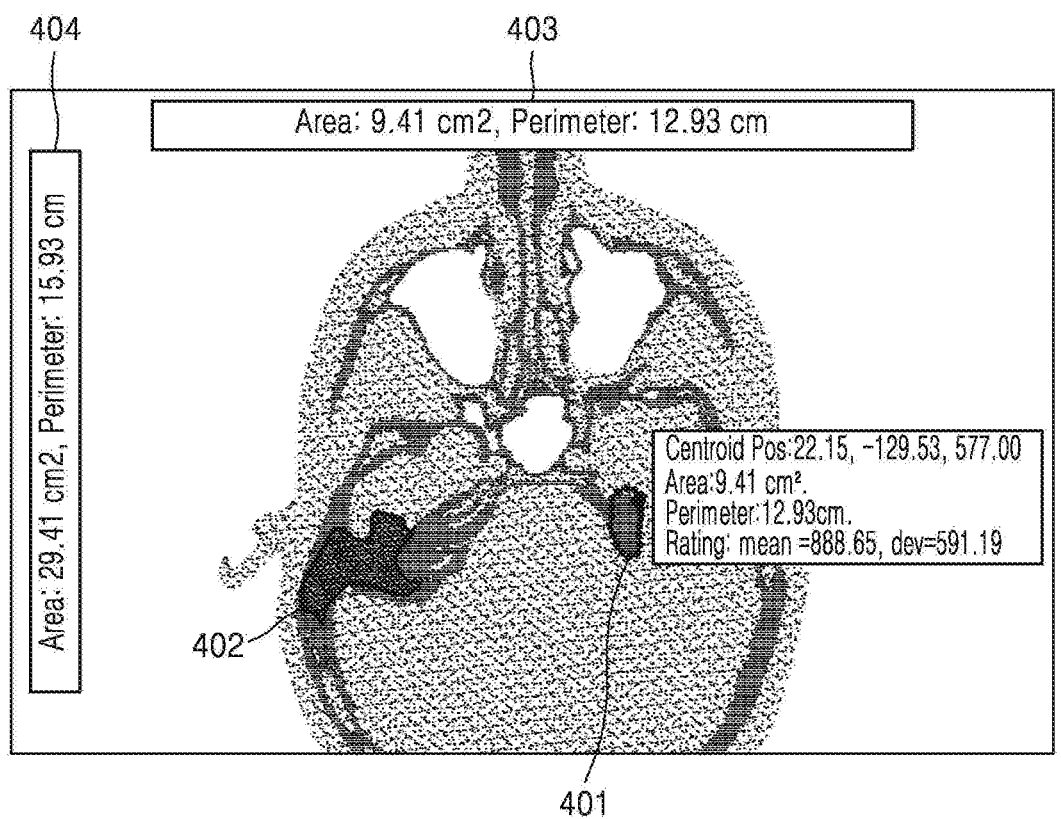
FIGS. 4A and 4B are views illustrating a method of displaying a medical image and geometry information of an object as a size of the medical image is changed, according to an example embodiment.
Figure 4B:
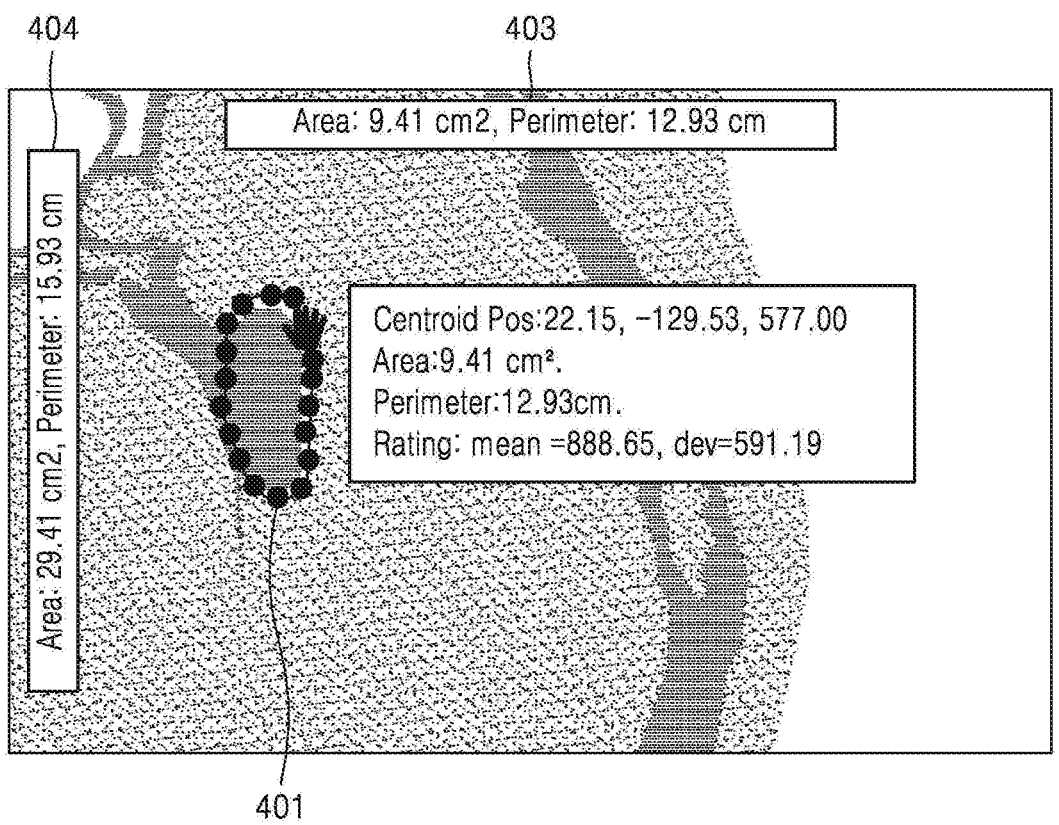

FIGS. 4A and 4B are views illustrating a method of displaying a medical image and geometry information of an object as a size of the medical image is changed, according to an example embodiment.

Referring to FIG. 4A, the apparatus 100 may display a first medical image of an object. The apparatus 100 may receive a user input that selects a region of interest, a portion of interest, or a point of interest of the object.

In detail, the apparatus 100 may receive an input that selects a first point and a second point in the first medical image, and may calculate a distance between the first point and the second point. Also, the apparatus 100 may calculate an angle between a first straight line that connects the first point and a reference point in the first medical image and a second straight line that connects the second point and the reference point.

Referring to FIG. 4A, the apparatus 100 may receive an input that selects a first object 401 and a second object 402 that are portions of interest of the object. The apparatus 100 may determine first geometry information 403 related to the first object 401 and second geometry information 404 related to the second object 402. Each geometry information may include any one or any combination of a size (e.g., a width) of the object, a length (e.g., a long diameter or a radius) of the object, and a position (e.g., an absolute position of the object or a relative position of the object) of the object, and it will be understood by one of ordinary skill in the art that other information related to the object may be further included.

The apparatus 100 may display the first geometry information 403 and the second geometry information 404 on a predetermined fixed region on a screen. For example, the predetermined fixed region may be set to any one or any combination of an upper portion, a lower portion, a left portion, and a right portion of the screen. In detail, as shown in FIG. 4A, the apparatus 100 may set the upper portion and the left portion on the screen as the predetermined fixed region in the form of a bar, and may display the first and second geometry information 403 and 404 on the bar.

FIG. 4B is a view illustrating a case in which a region corresponding to the first object 401 is enlarged and displayed in the first medical image of FIG. 4A. A user may enlarge and see a region of interest in a medical image. When the first medical image is enlarged and the region corresponding to the first object 401 is focused and displayed, the second object 402 or a third object that have been previously observed on the screen may not be displayed. In this case, the user has to reduce the first medical image to its original size or has to move the enlarged first medical image to see the second object 402 or the third object. When the region corresponding to the first object 401 is focused and displayed on the screen, the second object 402 may not be displayed on the screen. The second object 402 is an object that is located in the first medical image and is spaced by a predetermined distance apart from the first object 401. In this case, the apparatus 100 may display not only the first geometry information 403 of the first object 401 but also the second geometry information 404 of the second object 402 on the predetermined fixed region of the screen. The apparatus 100 may display the first geometry information 403 of the first object 401 and the second geometry information 404 of the second object 402 on different predetermined fixed regions.

Figure 5A:
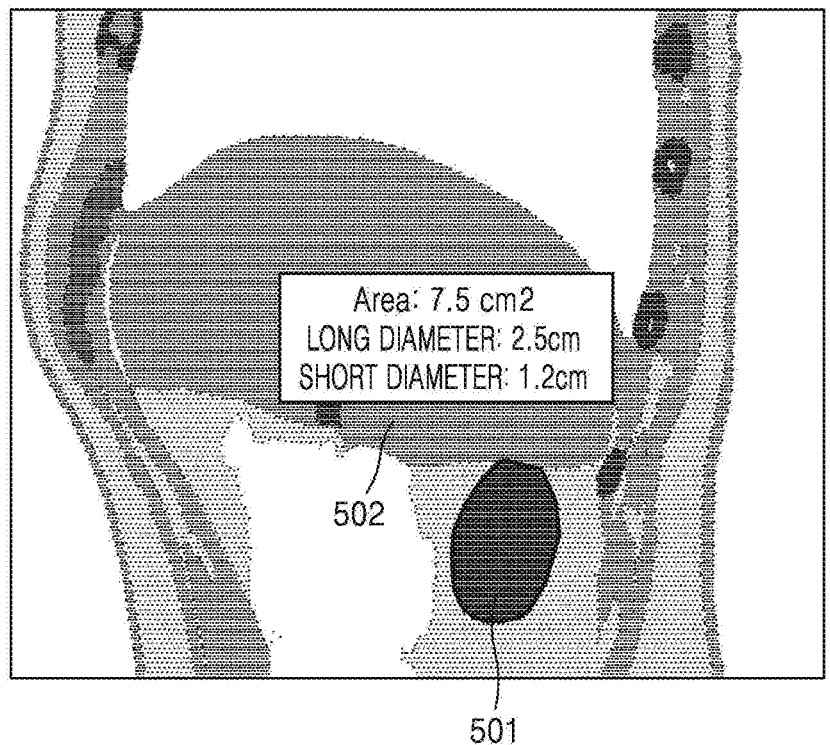
FIGS. 5A and 5B are views illustrating a method of displaying geometry information of an object according to whether the geometry information of the object may be displayed on a region adjacent to the object, according to an example embodiment.
Figure 5B:
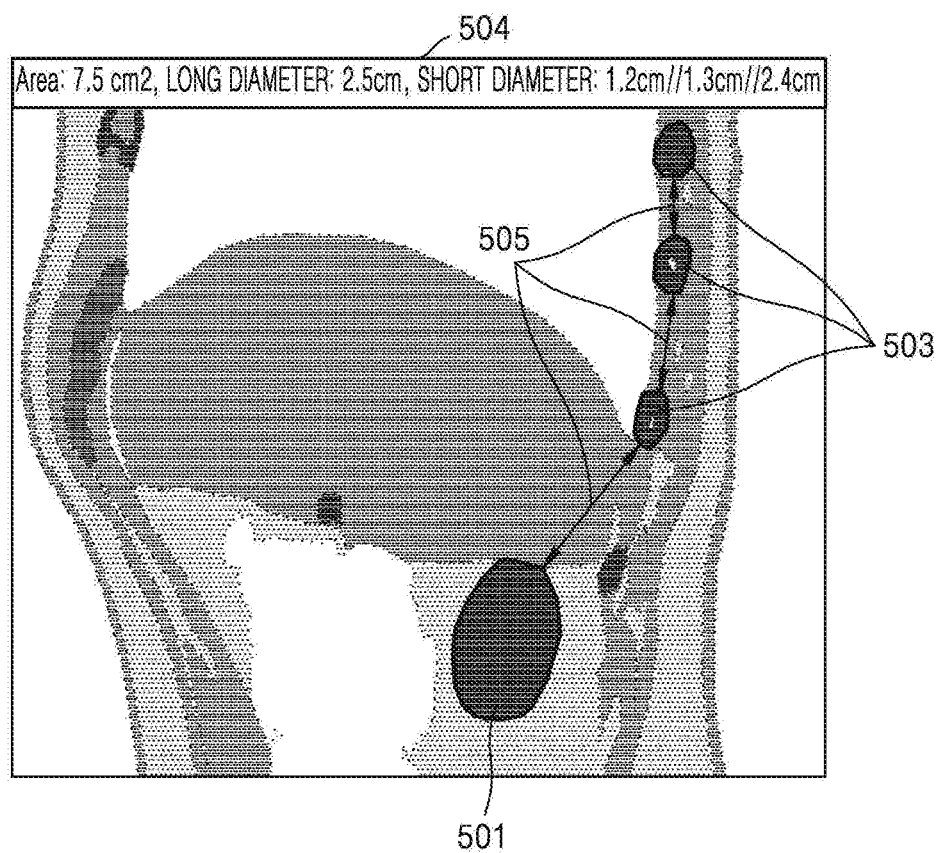

FIGS. 5A and 5B are views illustrating a method of displaying geometry information of an object according to whether the geometry information of the object may be displayed on a region adjacent to the object, according to an example embodiment.

When a region located adjacent to a first object 501 and large enough to display first geometry information exists in a first medical image, the apparatus 100 may control a predetermined fixed region to be removed from a screen, and may display the first geometry information to be displayed on the region adjacent to the first object 501. In this case, the apparatus 100 may also display the first geometry information even on the predetermined fixed region.

As shown in FIG. 5A, when a user selects only the first object 501 in the first medical image, as shown in a box 502, the apparatus 100 may display the first geometry information on the region adjacent to the first object 501, in consideration of a size of the region on which the first geometry information of the first object 501 is to be displayed on the screen and a relationship with neighboring objects around the first object 501.

When a region located adjacent to the first object 501 and large enough to display the first geometry information does not exist in the first medical image, the apparatus 100 may display the first geometry information on the predetermined fixed region.

As shown in FIG. 5B, when the user selects the first object 501 and second through fourth objects 503 in the first medical image, as shown in a bar 504, the apparatus 100 may display the first geometry information on the predetermined fixed region without superimposing the first geometry information in the first medical image, in consideration of a region on which geometry information of the first through fourth objects 501 and 503 is to be displayed on the screen and a relationship between the first through fourth objects 501 and 503 (e.g., a distance 505 between the first through fourth objects 501 and 503).

Figure 6:
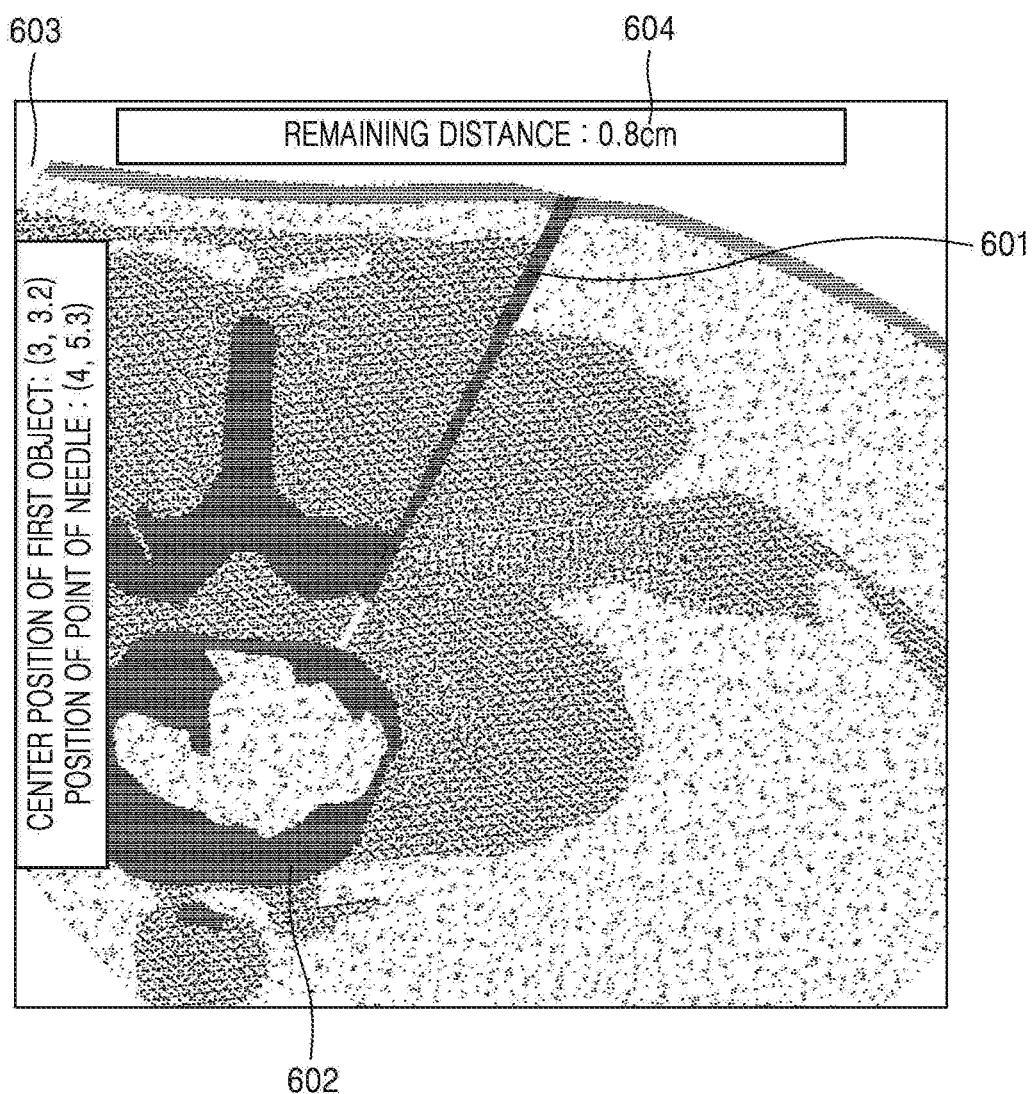
FIG. 6 is a view illustrating a method of displaying geometry information of an object in real time, according to an example embodiment.

FIG. 6 is a view illustrating a method of displaying geometry information of an object in real time, according to an example embodiment.

The apparatus 100 may display a medical image of an object in real time. As shown in FIG. 6, a user may inject a drug into a first object 602 of the medical image by using a needle 601. In this case, the apparatus 100 may track a position of the needle 601 in real time. Because the drug has to be accurately injected into the first object 602, the position of the needle 601 may be displayed.

The apparatus 100 may display position information of the needle 601 on an upper bar 604 and a left bar 603 that are fixed regions on a screen. As the needle 601 is moved in the object, the apparatus 100 may display updated position information of the needle 601 on the upper bar 604 and the left bar 603 of the screen.

Also, the apparatus 100 may display remaining distance information about a distance remaining until the needle 601 reaches the first object 602 or movement path information of the needle 601, on the upper bar 604 or the left bar 603.

Figure 7:
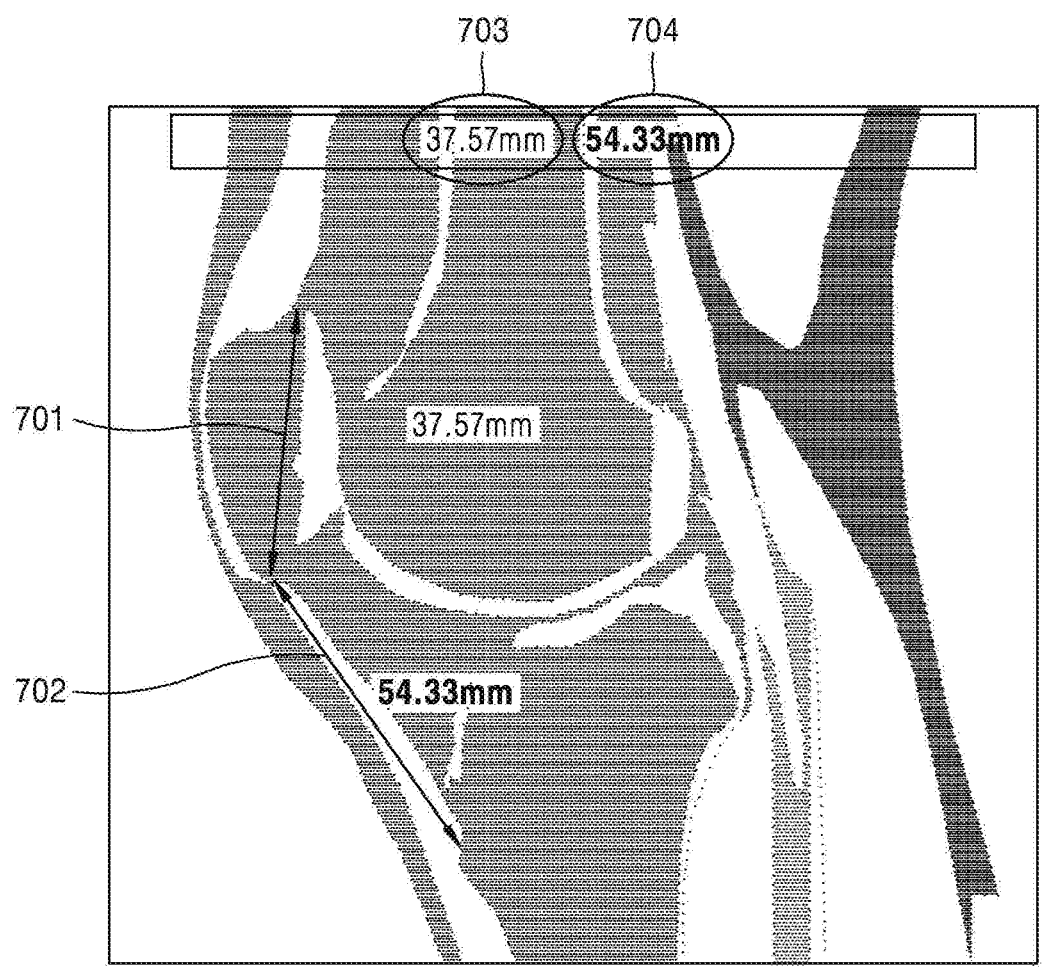
FIG. 7 is a view illustrating a method of displaying a plurality of pieces of geometry information in a medical image, according to an example embodiment.

FIG. 7 is a view illustrating a method of displaying a plurality of pieces of geometry information in a medical image, according to an example embodiment.

A user may select a plurality of objects as objects of interest in a medical image. The apparatus 100 may determine geometry information of each of the plurality of objects. The apparatus 100 may distinguishably display the geometry information of the plurality of objects on a predetermined fixed region.

As shown in FIG. 7, the apparatus 100 may calculate a distance 701 between a first point and a second point and a distance 702 between the first point and a third point. The apparatus 100 may distinguishably display distance information 703 between the first point and the second point and distance information 704 between the first point and the third point in different colors.

Figure 8:
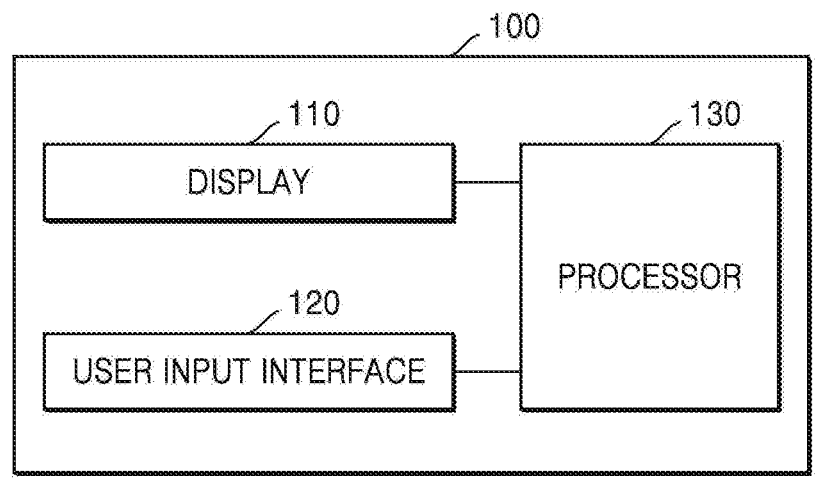
FIGS. 8 and 9 are block diagrams illustrating an apparatus for displaying a medical image, according to other example embodiments.
Figure 9:
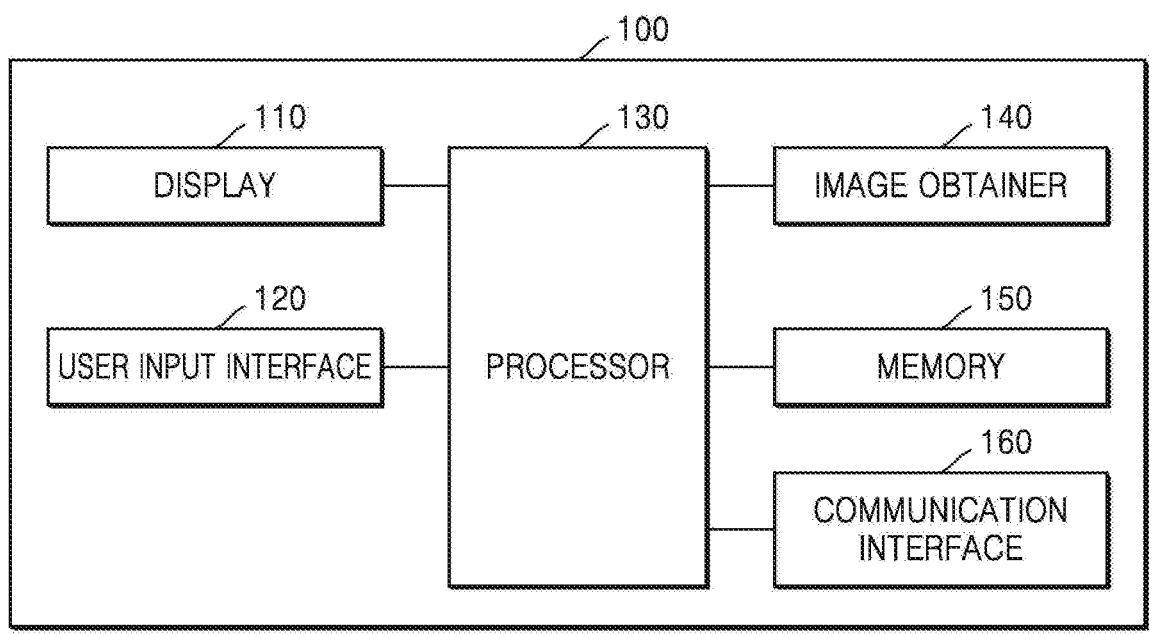

FIGS. 8 and 9 are block diagrams illustrating the apparatus 100 for displaying a medical image, according to other example embodiments.

As shown in FIG. 8, the apparatus 100 according to an example embodiment may include a display 110, a user input interface 120, and a processor 130. However, all elements illustrated in FIG. 8 are not essential elements. More or fewer elements than the elements illustrated in FIG. 8 may be included in the apparatus 100. For example, as shown in FIG. 9, the apparatus 100 according to an example embodiment may further include an image obtainer 140, a memory 150, and a communication interface 160 in addition to the display 110, the user input interface 120, and the processor 130.

The elements will now be described one by one.

The display 110 displays information processed by the apparatus 100. For example, the display 110 may display a medical image or a user interface (UI) or a GUI related to a control panel.

The display 110 may display the medical image of an object on a screen. The display 110 may display information related to a first object included in the object.

When the display 110 and a touchscreen have a layer structure and are configured as a touchscreen, the display 110 may be used as an input interface as well as an output device. The display 110 may include any one or any combination of a liquid crystal display (LCD), a thin-film transistor-liquid crystal display, an organic light-emitting diode, a flexible display, a 3D display, and an electrophoretic display. According to a type of the apparatus 100, the apparatus 100 may include two or more displays 110.

The user input interface 120 refers to an interface through which a user inputs data for controlling the apparatus 100. For example, examples of the user input interface 120 may include, but are not limited to, a key pad, a dome switch, a touchpad (e.g., a contact-type capacitance method, a pressure-type resistive overlay method, an infrared sensing method, a surface ultrasound transmission method, an integral tension measuring method, or a piezoelectric effect method), a track ball, and a jog switch. For example, the user input interface 120 may further include any of various input interfaces such as an electrocardiogram (ECG) measuring module, a respiration measuring module, a voice recognition sensor, a gesture recognition sensor, a fingerprint recognition sensor, an iris recognition sensor, a depth sensor, or a distance sensor.

The user input interface 120 may receive an input that selects the first object in a first medical image. Also, the user may adjust a size of the first medical image displayed on the screen through the user input interface 120, and may detect an object to be focused on the screen and control the determined object to be displayed at the center of the screen.

Also, the user input interface 120 may receive an input that zooms in on or zooms out from the first object. Also, the user input interface 120 may receive an input that controls the first medical image to be moved on the screen or an input that controls the screen to be changed from the first medical image to a second medical image. The display 110 may display the first medical image on the screen, based on the control input received from the user input interface 120.

The processor 130 controls an overall operation of the apparatus 100. For example, the processor 130 may control the display 110, the user input interface 120, the image obtainer 140, the memory 150, and the communication interface 160.

The processor 130 may determine first geometry information including either one or both of position information and size information of the first object. The processor 130 may control the first geometry information to be displayed on a predetermined fixed region on the screen. The predetermined fixed region may not be affected by an input that controls a zoom level with respect to the first object, an input that controls the first medical image to be moved on the screen, and an input that controls the screen to be changed from the first medical image to the second medical image. Also, the predetermined fixed region may be preset by the user. Also, the predetermined fixed region may be any one or any combination of an upper portion, a lower portion, a left portion, and a right portion of the screen. For example, the predetermined fixed region may be an upper portion and a left portion of the screen.

The position information of the first object may include any one or any combination of relative position information between a reference position and a position of the first object in the first medical image, relative position information between the first object and a neighboring object around the first object, and absolute position information of the first object.

Also, when a region located adjacent to the first object and large enough to display the first geometry information exists in the first medical image, the processor 130 may control the predetermined fixed region to be removed and may control the first geometry information to be displayed on the region adjacent to the first object. The display 110 may display the predetermined fixed region on the region adjacent to the first object in the first medical image without displaying the predetermined fixed region on the screen. Alternatively, the processor 130 may display the first geometry information on both the predetermined fixed region and the region adjacent to the first object, without removing the predetermined fixed region.

When the first medical image is enlarged on the screen and the whole or a part of the first object is not displayed on the screen, the display 110 may continuously display the first geometry information on the predetermined fixed region.

Also, the processor 130 may adjust the amount of display of the first geometry information, based on a degree to which the first medical image is enlarged on the screen.

As the first object is moved in the object, the display 110 may display updated first geometry information on the predetermined fixed region.

When a plurality of the predetermined fixed regions exist, the display 110 may distribute the first geometry information and may display the distributed first geometry information on the plurality of regions according to a preset standard. The preset standard may be set, but not limited to, so that the position information of the first object is displayed on a first predetermined region among the plurality of regions and the size information of the first object is displayed on a second predetermined region among the plurality of regions.

The user input interface 120 may receive an input that selects a second object in the first medical image. The processor 130 may determine second geometry information of the second object. The display 110 may display the second geometry information of the second object on the predetermined fixed region so that the second geometry information of the second object is distinguished from the first geometry information of the first object.

The image obtainer 140 may obtain the medical image of the object. For example, the image obtainer 140 may transmit an ultrasound signal to a predetermined portion in a body from a surface of the object, and may obtain an ultrasound image of the object by using information about the ultrasound signal reflected from tissue in the body.

Also, the image obtainer 140 may obtain a cross-sectional image (e.g., an MR image) of the object by expressing an intensity of an MR signal to an RF signal generated in a magnetic field with an intensity as a contrast. The image obtainer 140 may obtain a CT image or an X-ray image by emitting X-rays to the object.

The image obtainer 140 may obtain the first medical image and the second medical image including the first object. The processor 130 may determine the first geometry information of the first object in the first medical image and the second geometry information of the first object in the second medical image. The processor 130 may synthesize the first medical image and the second medical image, based on the determined first geometry information and the determined second geometry information, to obtain a synthesized medical image. The display 110 may display the synthesized medical image.

The memory 150 may store a program for processing of the processor 130, and may store input/output data (e.g., medical image data, information about a person to be examined, probe information, and a body marker).

The memory 150 may include at least one storage medium among a flash memory, a hard disk, a multimedia card micro-type memory, a card-type memory (e.g., an SD or XD memory), a RAM, a static random-access memory (SRAM), a ROM, an electrically erasable programmable read-only memory (EEPROM), a programmable read-only memory (PROM), a magnetic memory, a magnetic disk, and an optical disk. Also, the apparatus 100 may operate a web storage or a cloud server that performs a storage function of the memory 150 on the Internet.

The communication interface 160 may include one or more elements through which the apparatus 100 and a server or the apparatus 100 an external device may communicate with each other. For example, the communication interface 160 may include a short-range communication module, a wired communication module, or a mobile communication module.

The short-range communication module refers to a module for short-range communication within a predetermined distance. Examples of short-range communication technology may include Wi-Fi, Bluetooth, Bluetooth Low Energy (BLE), Ultra-Wideband (UWB), ZigBee, Near-Field Communication (NFC), Wi-Fi Direct (WFD), and Infrared Data Association (IrDA).

The wired communication module refers to a module for communication using an electrical signal or an optical signal. Examples of wired communication technology may include a pair cable, a coaxial cable, an optical fiber cable, and an Ethernet cable.

The mobile communication module transmits/receives a wireless signal to/from any one or any combination of a base station, an external device, and a server through a mobile communication network. Examples of the wireless signal may include a voice call signal, a video call signal, and any of various types of data through text/multimedia message transmission/reception.

The communication interface 160 is connected to a network by wire or wirelessly and communicates with an external device. The communication interface 160 may transmit and receive data to and from a hospital server or another medical apparatus in a hospital connected through a PACS. Also, the communication interface 160 may exchange data according to the DICOM standard.

The communication interface 160 may transmit/receive data (e.g., medical image data of the object) related to diagnosis of the object through the network, and may also transmit/receive a medical image obtained by another medical apparatus. Furthermore, the communication interface 160 may receive information about a diagnosis history or a treatment schedule of a patient from a server and may use the information to diagnose the object.

The apparatus 100 may be realized in the form of a hardware component, a software component, and/or a combination of a hardware component and a software component. For example, the device and corresponding components according to the above-described example embodiments may be realized by using at least one or more universal computers or special-purpose computers, such as a processor, a controller, an arithmetic logic unit (ALU), a digital signal processor, a micro-computer, a field-programmable array (FPA), a programmable logic unit (PLU), a microprocessor, or any type of device that may execute and respond to an instruction (or command).

The software may include a computer program, a code, an instruction, or a combination of one or more of the above items. And, the software may configure a processing device, so that the processing device may be operated as intended, or the software may independently or collectively instruct (or command) the processing device.

To be interpreted by the processing device, or to provide an instruction or data to the processing device, the software and/or data may be permanently or temporarily embodied in any type of machine, a component, a physical device, virtual equipment, a computer storage medium or device, or a transmitted signal wave. Because the software is dispersed (or scattered) within a computer system being connected to a network, the software may be stored or executed by using in a dispersion method. The software and data may be stored in one or more computer-readable recording media.

It will be apparent to one of ordinary skill in the art that various modifications and variations may be made in the present disclosure without departing from the spirit or scope of the present disclosures. For example, the above-described techniques may be executed in an order different from that described in the description of the present disclosure, and/or the components of the above-described system, structure, equipment (or device), circuit, and so on, may be combined in a format different that of the above-described method according to the present disclosure, and an adequate result may be achieved even if the above-described components of the present disclosure are replaced by any other component or its equivalent.

The scope of the present disclosure is not defined by the detailed description of the present disclosure but by the claims and equivalents thereof.

What is claimed is:

1. A method of displaying a medical image, the method comprising:
    displaying a first medical image on a screen, based on a first input that zooms in on or zooms out from a first object in the first medical image;
    determining first geometry information comprising either one or both of position information and size information of the first object;
    determining whether an adjacent region located adjacent to the first object and large enough to display the first geometry information exists in the first medical image;
    displaying the first geometry information as text information on the adjacent region exist in the first medical image; and
    displaying the first geometry information on the predetermined fixed region of the screen in response to the adjacent region being determined not to exist in the first medical image,
    wherein the displaying of the first geometry information comprises, in response to the first input that zooms in on or zooms out from the first object in the first medical image, continuously displaying the first geometry information on the predetermined fixed region while a zoom level of the first medical image changes.

2. The method of claim 1, wherein the predetermined fixed region is not affected by a second input that controls a zoom level with respect to the first object, a third input that controls the first medical image to be moved on the screen, and a fourth input that controls the screen to be changed from the first medical image to a second medical image.

3. The method of claim 1, wherein the displaying of the first geometry information comprises, based on the first medical image being enlarged on the screen and a whole or a part of the first object not being displayed on the screen, continuously displaying the first geometry information on the predetermined fixed region.

4. The method of claim 1, wherein the displaying of the first geometry information comprises, as the first object is moved in real time, updating the first geometry information, and displaying the first geometry information that is updated, on the predetermined fixed region.

5. The method of claim 1, wherein the predetermined fixed region comprises any one or any combination of an upper portion, a lower portion, a left portion, and a right portion of the screen, and
    wherein, based on the predetermined fixed region comprising a plurality of predetermined fixed regions, the displaying of the first geometry information comprises displaying the first geometry information respectively on the plurality of predetermined fixed regions, according to a preset standard.

6. The method of claim 5, wherein the preset standard is set so that the position information of the first object is displayed on a first predetermined region among the plurality of predetermined fixed regions, and the size information of the first object is displayed on a second predetermined region among the plurality of predetermined fixed regions.

7. The method of claim 1, further comprising:
    obtaining a second medical image comprising the first object;
    determining second geometry information of the first object in the second medical image;
    obtaining a synthesized medical image by synthesizing the first medical image and the second medical image, based on the first geometry information of the first object in the first medical image and based on the second geometry information of the first object in the second medical image; and
    displaying the synthesized medical image.

8. The method of claim 1, further comprising:
    receiving a second input that selects a second object in the first medical image;
    determining second geometry information of the second object; and
    displaying, along with the first geometry information, the second geometry information of the second object on the predetermined fixed region so that the second geometry information of the second object is distinguished from the first geometry information of the first object.

9. An apparatus for displaying a medical image, the apparatus comprising:
    a display configured to display a first medical image on a screen;
    a user input interface configured to receive a first input that zooms in on or zooms out from a first object in the first medical image that is displayed; and
    a processor configured to:
        control the display to display the first medical image on the screen, based on the first input;
        determine first geometry information comprising either one or both of position information and size information of the first object;
        determine whether an adjacent region located adjacent to the first object and large enough to display the first geometry information exists in the first medical image;
        control the display to display the first geometry information as text information on the adjacent region instead of a predetermined fixed region, in response to the adjacent region being determined to exist in the first medical image, and
        control the display to display the first geometry information on the predetermined fixed region of the screen in response to the adjacent region being determined not to exist in the first medical image,
    wherein the processor is further configured to, in response to the first input that zooms in on or zooms out from the first object in the first medical image, control the display to continuously display the first geometry information on the predetermined fixed region while a zoom level of the first medical image changes.

10. The apparatus of claim 9, wherein the predetermined fixed region is not affected by a second input that controls a zoom level with respect to the first object, a third input that controls the first medical image to be moved on the screen, and a fourth input that controls the screen to be changed from the first medical image to a second medical image.

11. The apparatus of claim 9, wherein the position information of the first object comprises any one or any combination of relative position information between a reference position and a first position of the first object in the first medical image, relative position information between the first object and a neighboring object around the first object, and absolute position information of the first object.

12. The apparatus of claim 9, wherein the processor is further configured to, based on the first medical image being enlarged on the screen and a whole or a part of the first object not being displayed on the screen, control the display to continuously display the first geometry information on the predetermined fixed region.

13. The apparatus of claim 9, wherein the processor is further configured to adjust an amount of the first geometry information that is displayed, based on a degree to which the first medical image is enlarged on the screen.

14. The apparatus of claim 9, wherein the processor is further configured to, as the first object is moved in real time, update the first geometry information, and control the display to display the first geometry information that is updated, on the predetermined fixed region.

15. The apparatus of claim 9, wherein the predetermined fixed region comprises any one or any combination of an upper portion, a lower portion, a left portion, or a right portion of the screen, and
wherein the processor is further configured to, based on the predetermined fixed region comprising a plurality of predetermined fixed regions, control the display to display the first geometry information respectively on the plurality of predetermined fixed regions, according to a preset standard.

16. The apparatus of claim 9, wherein the user input interface is further configured to receive a second input that selects a second object in the first medical image, and
wherein the processor is further configured to:
determine second geometry information of the second object; and
control the display to display, along with the first geometry information, the second geometry information of the second object on the predetermined fixed region so that the second geometry information of the second object is distinguished from the first geometry information of the first object.

17. A non-transitory computer-readable medium storing instructions executable by a processor of an apparatus for displaying a medical image, to cause the processor to:
display the medical image on a screen;
in response to receiving a first selection of a first object and a second object in the medical image that is displayed, display, along with the medical image, geometry information of the first object and the second object, on a predetermined fixed region of the screen;
in response to receiving an input that zooms in on the first object in the medical image that is displayed along with the geometry information of the first object and the second object, enlarge the medical image that is displayed, display the first object in the medical image that is enlarged, and cease display of the second object in the medical image that is displayed; and
continuously display the geometry information of the first object and the second object on the predetermined fixed region while a zoom level of the medical image increases;
determine whether an adjacent region located adjacent to the first object and large enough to display the geometry information exists in the medical image; and
display the geometry information as text information on the adjacent region instead of the predetermined fixed region, in response to the adjacent region being determined to exist in the medical image.

18. The non-transitory computer-readable medium of claim 17, wherein the geometry information comprises either one or both of a remaining distance until the second object reaches the first object and a movement path of the second object.

19. The non-transitory computer-readable medium of claim 17, wherein the instructions are executable by the processor to further cause the processor to, in response to receiving a second selection of a third object in the medical image that is displayed, display, along with the medical image, a first distance between the first object and the second object and a second distance between the second object and the third object, on the predetermined fixed region of the screen.

* * * * *